United States Patent [19]

Engel et al.

[11] Patent Number: 4,631,295
[45] Date of Patent: Dec. 23, 1986

[54] FUNCTIONAL OIL-CREAM BATH

[75] Inventors: Walter Engel, Pinneberg; Udo Hoppe, Hamburg; Gerhard Sauermann, Wiemersdorf, all of Fed. Rep. of Germany

[73] Assignee: Beiersdorf Aktiengesellschaft, Hamburg, Fed. Rep. of Germany

[21] Appl. No.: 736,749

[22] Filed: May 22, 1985

Related U.S. Application Data

[63] Continuation of Ser. No. 582,370, Feb. 22, 1984, abandoned.

[30] Foreign Application Priority Data

Mar. 2, 1983 [DE] Fed. Rep. of Germany ....... 3307297

[51] Int. Cl.⁴ .............................................. A61K 31/20
[52] U.S. Cl. .................................................... 514/558
[58] Field of Search ......................................... 514/558

[56] References Cited

U.S. PATENT DOCUMENTS 3,867,300 2/1975 Karabinos et al. ................. 252/106
4,246,285 1/1981 Van Duzee .......................... 424/358

FOREIGN PATENT DOCUMENTS

A1337769 5/1961 France .
A2293924 7/1976 France .

OTHER PUBLICATIONS

Chem. Absts. 94 (1981), 109371p (Yasunishi, Kosaku).
Wells & LuBowe—"Cosmetics of the Skin", Reinhold Pub. (Textbook), 1964, pp. 333–341.

*Primary Examiner*—Leonard Schenkman
*Attorney, Agent, or Firm*—Sprung Horn Kramer & Woods

[57] ABSTRACT

The present invention relates to an oil-cream bath that, added in a conventional amount to the bath water, lends it not only a skin-care and fat-restoration action but also a regenerating and normalizing effect on the skin, especially in the existence of non-clinical deviations from the norm, aging skin for example.

18 Claims, No Drawings

FUNCTIONAL OIL-CREAM BATH

This is a continuation of application Ser. No. 582,370 filed Feb. 22, 1984 now abandoned.

BACKGROUND OF THE INVENTION

The present invention relates to an oil-cream bath that, added to a conventional amount of the bath water, not only has a cosmetic action in that it makes the skin soft, silky, and smooth, the action remains long after the application, but also can bring about a regenerating and normalizing effect on the skin.

Tub and shower baths to which appropriate bath preparations (bath-additive preparations) are added are enjoying increasing popularity among consumers because they not only serve to cleanse the body but also promote a feeling of cleanliness, relaxation, and refreshment during the bath that is of considerable significance for the physiological and psychological effect of the bath on the total organism.

Possible externally applied preparations that have an effect on the skin include in particular bath preparations based on lipids. Baths of this type can apply lipids to the skin. Since the beneficial effect of lipids in protecting the skin and in normalizing the condition of the skin, especially dry skin, has, on the other hand, been known for a long time, oil baths have often been applied for the purpose of applying lipids to low-fat skin, with the cleansing action often occupying a backround position.

It is known that even a simple water bath, a bath, that is, without the addition of a preparation developed for this purpose, will lead to structural and functional alterations in the film on the surface of the skin. This interaction product consists chemically of the cutaneous-layer materials, of the keratinization of the epithelial cells, of the polar water-soluble skin-content materials, of the non-polar lipid-soluble sebum with its complicated composition, and of water, which occurs both free and bound. It represents a complex and closed physiological system.

Even in a simple (pure) water bath without any additive, the first that occurs is a swelling of the cutaneous layer that depends of the length of the bath and its temperature. Water-soluble materials in the surface of the skin (water-soluble dirt for example), but also materials that are responsible for the water-binding capacity of the cutaneous layer, are simultaneously removed by being dissolved. There occurs simultaneously as the result of emulsifiers inherent in the body also a certain amount of fat dissolution. This later causes, subsequent to the initial swelling, a definite drying of the skin that is augmented even more by wash-active additives, especially in the direction of defatting. The natural equilibrium of the content materials is accordingly disrupted and the remaining material alters its properties. Finally, the hydration potential of the skin-surface film is perceptibly decreased.

If the skin is intact, this damage is unimportant. The protective mechanisms of the skin have no problem in compensating for such slight impairments in the upper skin layers. Even when non-pathological deviations, like environmentally determined wear and tear or irritations, sunburn, elderly skin etc. for example are present however, the protective mechanism of the skin-surface film is disrupted and thus often incapable of carrying out its assignment by itself. It must then be regenerated by external means.

In looking through the published recipes for known cosmetic bath preparations, it is evident that they mostly consist of simple mixtures of lipids—such as fats, that is, waxy esters, higher alcohols, hydrocarbons, and similar materials, each used by itself alone or in combinatins. The properties of these fatty or oily phases are varied in accordance with the purpose for which they are intended by the addition of surface-active substances selected from the aspect of obtaining the least possible defatting effect with a relatively satisfactory cleansing action. Thus, compounds (bath-additive preparations) can be formulated in accordance with the type and amount of constituents selected that will produce either films of oil that spread over the surface of the bath water, emulsions of oil in water, or even total solubilizates, with both foaming and non-foaming formulations being possible. Although outstanding effects on the skin that can still be objectively evaluated by biophysical measurement of the skin, parameters can in many cases be obtained even with the known bath-additive preparations, considering their relatively simple composition, the functionality of such formulations in oil or oil-cream bath preparations has been limited up to now only to adding, restoring, or supplying excess fat to the uppermost skin layers.

Attempts to develop functional oil-cream baths with a performance that would extend beyond a skin-care and fat-restoring effect, have always been unsatisfactory up to now and have not led to the desired results when used. In this case it must not be overlooked and in aggravating to observe that the conventional practical concentration of a bath-additive preparation in a bath results in a dilution of bath additive to water of 1:5000. For 100 liters (1) of bath water, for instance, and at a hardness range of 3 (2.5–3.8 mmol/1GH*), a chemical reactivity of 15–21 g of overall hardness elements calculated in the form of CaO must be counted on. The generally mild alkaline reaction of water is known.

*GH=gesteintharte (=overall hardness of water)

SUMMARY OF THE INVENTION

The object of the present invention is to develop a functional oil-cream bath that, added in a conventional amount to the bath water, in addition to a skin-regenerating effect simultaneously has a skin-care and fat-restoration effect. "Skin regeneration" is to be understood in the sense of the restoration and reintroduction of the skin to a healthy state with its associated special properties.

The object of the invention is accordingly a functional ol-cream bath containing pelargonic acid (n-nonylic acid) as an active ingredient in addition to the constituents that are conventional in such products.

The amount of pelargonic acid added to the oil-cream bath can range from 0.5 to 70%, preferably, however, from 0.5 to 11% by weight, and especially from 2 to 5% by weight by weight of the overall composition of the preparation.

Because of its particular status, of the biological data, and of its physical and chemical properties, pelargonic acid alone of all similarly structured compounds can satisfy all the prerequisites with respect to suitability for the special application in accordance with the invention. This has been demonstrated by means of appropriate comparative tests.

The use of acids or acidic buffer mixtures to affect skin parameters is generally known. Subject to the conditions of a water bath, however, the use of acids (with the exception of carbonic-acid baths) has been associated with dermatological or toxicological drawbacks for very many reasons. The use of pelargonic acid in oil-cream baths, on the other hand, eliminates these drawbacks to the widest possible extend because its combinations of valuable properties—like the low but measurable solubility of pelargonic acid in water, its very satisfactory and preferred solubility in lipids, its weak chemical reactivity, which is nevertheless satisfactory for the purpose, its lipid nature, its pH in a concentrated aqueous solution, which is in the physiological range, its antimicrobial properties, the possible mixture of the pelargonate with the hardness elements in the water with its resulting cosmetic properties, its satisfactory capacity for supplying protons to stabilize skin pH, and the lack of effect on the part of the pH of the water—all come to the fore in this special application in a very practical way.

What is, however, especially decisive for its effectiveness is the coefficient of distribution of pelargonic acid in oil to water. This means in practice that the outstanding and preferred solubility of pelargonic acid in the lipid phase of the bath preparation accompanied by minimum migration out into the aqueous phase must be ensured by appropriate formulation. Baths of this type promote controlled release of one or more cosmetically active substances.

The oil-cream bath preparations in accordance with the invention contain about 75 to 90% oily material (lipids), preferably in the form of vegetable oils like soybean oil, sesame-seed oil, peanut oil, sunflower oil, cotton-seed oil, and castor oil, which can be used individually or mixed together. These vegetable oils can be replaced entirely or partly by mineral oils (white pharmaceutical oils of high quality like paraffin and Vaseline oils). The preparations may also contain small amounts of natural or synthetic esters like isopropyl myristate, isopropyl palmitate, decyloleate, or even 2-octyldodecyl alcohol as fat restorers and solutizers or softeners as well as lanolin derivatives and cholesterol derivatives and perfume oils and other substances that are not soluble in water and that have antiseptic, bactericidal, or bacteriostatic properties in the amounts that are conventional in such preparations.

The oil-cream bath preparations runoff in accordance with the invention preferably contains up to 12% (especially 0.5 to 12%) by weight of the total composition of a polyethylene-glycol mono- or diester or other emulsifier. Polyethylene glycol (400) dioleate as proved especially practical. They may also contain alkylether sulfates like amino-neutralized lauryl ether sulfate for example as additional surface-active agents that exhibit satisfactory foaming when used in the form of their salts, even when highly diluted and in hard industrial water, and are distinguished by an excellent fat and lime-soap dispersing capacity. The constituents, all of which must be non-toxic and non-irritating, must be selected such that the oily proportion will be as high as possible and that of the emulsifiers and surface-active substances as low as possible. Furthermore, it is essential to maintain an extensive viscosity on the part of the oil-cream bath over the widest possible range of temperatures.

The relatively high proportion of vegetable oils in the oil-cream bath in accordance with the invention necessitates the addition of a preservative or antioxidant in the amount conventional for compounds of the type. It must be taken into consideration that these amount must also be sufficient to prevent microbial spoilage of the product during storage and shipping and during possession by the consumer. Benzoates*, benzoic-acid derivatives, sorbates*, and compounds like 2,6-di-tert-butyl-4-methylphenol (Ionol) or 5-bromo-5-nitro-1,3-dioxane can be added for this purpose. The oil-cream bath may also contain colorants and thickeners.

*like sodium benzoate
**especially p-hydroxybenzoic acid-loweralkyl- or benzylesters
***for example (alkali sorbates) The amount of perfume and if necessary colorants and thickeners to be applied in each case can easily be determined in accordance with the specific composition of the product by means of simple test conducted by one skilled in the art.

The oil-cream bath in accordance with the invention is manufactured by conventional methods by simply mixing the constituents while gently stirring. There are no problems involved.

Test were conducted to demonstrate the superiority of the oil-cream bath containing pelargonic acid in accordance with the invention over a known oil of identical composition but without the additive. The effects of the bathing process and its regulation by means of oil or oil-cream bath additives on the pH of the surface of the skin were measured. Subjects who belonged to the target group of "those in need of oil baths" were selected from an overall group of 20. These volunteers, with rather lipid-poor and dry skin, had a mean age of 48 years ($s^*=5.7$ $a^o$; $N^{**}=10$) and a mean skin lipid content $E=0.227$ ($s=0.095$; $N=56$, with the value for pronounced dry skin being E 0.25). It was found that, immediately subsequent to bathing with municipal water, the acidity of the test areas of the surface of the skin had decreased highly significantly (with 99.9% certainty, paired comparison) from a mean pH 5.24 to levels ranging from pH 5.8 to 6.0. This relative alkalization of the skin is adjusted toward the initial value (back-regulation) in a skin counterreaction lasting several hours. Adding the oil bath without pelargonic acid and the oil-cream bath with pelargonic acid (2.5% of the overall formulation) in accordance with the invention in equal amounts to the baths employing municipal water demonstrated that skin-pH regulation 45 minutes after leaving the bath is definitely significantly better in the case of the oil-cream bath containing pelargonic acid than that of a strictly water bath or of a bath treated with the known oil bath. The half-value times determined for the back-regulation of the pH to its initial level were over 3 hours for the strictly municipal-water bath, about 50 minutes for a municipal-water bath treated with a conventional oil-bath additive, and only 20 minutes for a municipal-water bath treated with an oil-cream bath additive containing pelaragonic acid in accordance with the invention. The superiority of the oil-cream bath in accordance with the invention over ordinary known oil baths is definitely obvious from the results of these tests.

*s=standard deviation
**N=number of volunteers
$^o$a=years (annum)

The following examples will describe the invention in greater detail without limiting it in any way.

EXAMPLE 1

|  | % by weight |
| --- | --- |
| Soybean oil | 38.75 |
| Castor oil | 2.00 |

-continued

| | % by weight |
|---|---|
| Vaseline oil | 37.00 |
| Pelargonic acid | 2.50 |
| 2-octyldodecanol | 2.00 |
| Polyethylene-glycol(400) dioleate | 10.00 |
| Adjuvants, colorants, perfume (Stabilizers) | ad 100.00 |

EXAMPLE 2

| | % by weight |
|---|---|
| Walnut oil | 40.00 |
| Paraffin oil | 40.00 |
| Pelargonic acid | 5.00 |
| Polyethylene-glycol(400) dioleate | 12.00 |
| Adjuvants, colorants, perfume | ad 100.00 |

What is claimed is:

1. In a cosmetic regenerating and normalizing oil-cream bath preparation containing pelargonic acid, an active ingredient and an inert cosmetic carrier, the improvement wherein the active ingredient contains 0.5 to 5.0% weight of pelargonic acid.

2. An oil-cream bath preparation of claim 1 containing 2 to 5% by weight pelargonic acid and an inert cosmetic carrier.

3. An oil-cream bath preparation of claim 1 which is about 75-90% by weight lipids.

4. An oil-cream bath preparation of claim 3 which is about 80-90% by weight lipids.

5. An oil-cream bath preparation of claim 3 containing about 10 to 12% by weight emulsifier.

6. An oil-cream bath preparation of claim 3 in which the lipid is a vegetable and/or mineral oil.

7. A cosmetic regenerating and normalizing oil-cream bath according to claim 6, wherein the vegetable oil is selected from the group consisting of soybean oil, sesame-seed oil, peanut oil, sunflowe oil, cotton-seed oil and castor oil.

8. A cosmetic regenerating and normalizing oil-cream bath according to claim 6, wherein the mineral oil is white pharmaceutical oil.

9. An oil-cream bath preparation of claim 1 containing about 0.5-12% by weight emulsifier.

10. An oil-cream bath preparation of claim 9 in which the emulsifier is a polyethylene-glycol mono- or di-ester.

11. An oil-cream bath preparation of claim 10 in which the emulsifier is polyethylene-glycol (400)-dioleate.

12. A cosmetic regenerating and normalizing oil-cream bath preparation of claim 1 comprising (a) 0.5 to 5.0% by weight of pelargonic acid; (b) vegetable and/or mineral oil; and (c) an emulsifier.

13. A cosmetic regenerating and normalizing oil-cream bath preparation of claim 1 consisting essentially of 0.5 to 5.0% by weight of pelargonic acid, 75 to 90% by weight of vegetable and/or mineral oil, and 0.5 to 12% by weight of an emulsifier.

14. A cosmetic regeneration a normalizing oil-cream bath preparation according to claim 1, further comprising one or more auxiliary compounds selected from the group consisting of fat restorers, softeners, bactericides, surface-active agents, preservatives, antioxidants, colorants, thickeners and perfume oils.

15. A cosmetic regeneration and normalizing oil-cream bath according to claim 1, which further comprises esters selected from the group consisting of isopropyl myristate, isopropyl palmitate and decyloleate and 2-octyldodecyl alcohol.

16. A cosmetic regeneration and normalizing oil-cream bath preparation according to claim 1 comprising 38.75 weight % soybean oil, 2.00 weight % castor oil, 37 weight % Vaseline oil, 2.50 weight % pelargonic acid, 2.00 weight % 2-octyldodecanol, 10 weight % polyethylene-glycol (400) dioleate.

17. A cosmetic regenerating and normalizing oil-cream bath according to claim 1, comprising 40.00 weight % walnut oil, 40.00 weight % paraffin oil, 5.00 weight % pelargonic acid, and 12.00 weight % polyethylene-glycol (400) dioleate.

18. A method of imparting a skin-regeneration effect on the skin of a warm-blooded animal patient comprising contacting the skin of said patient with a water bath containing an effective amount of the oil-cream bath preparation of claim 1.

* * * * *